United States Patent [19]

Hanaoka et al.

[11] Patent Number: 4,584,276

[45] Date of Patent: Apr. 22, 1986

[54] METHOD FOR ANALYSIS OF ANIONS

[75] Inventors: Yuzuru Hanaoka; Takeshi Murayama; Setsuo Muramoto; Tamizo Matsuura, all of Tokyo, Japan

[73] Assignee: Yokogawa Hokushin Electric Corporation, Tokyo, Japan

[21] Appl. No.: 701,996

[22] Filed: Feb. 15, 1985

Related U.S. Application Data

[62] Division of Ser. No. 385,570, Jun. 7, 1982, Pat. No. 4,533,518.

[30] Foreign Application Priority Data

Feb. 5, 1982 [JP] Japan ................................. 57-17121

[51] Int. Cl.[4] ..................... G01N 30/14; G01N 30/96; B01D 13/00
[52] U.S. Cl. ................................. 436/150; 73/61.1 C; 210/649; 210/656; 422/70; 436/161; 436/175; 436/178
[58] Field of Search ........................ 422/68, 69, 70; 436/150, 161, 175, 176, 177, 178; 73/61.1 C; 210/198.2, 321.1, 649, 656, 659

[56] References Cited

U.S. PATENT DOCUMENTS

| | | | |
|---|---|---|---|
| 3,926,559 | 12/1975 | Stevens | 436/161 X |
| 4,314,823 | 2/1982 | Rich et al. | 436/177 X |
| 4,403,039 | 9/1983 | Ban et al. | 422/70 X |

FOREIGN PATENT DOCUMENTS

| | | | |
|---|---|---|---|
| 0032770 | 7/1981 | European Pat. Off. | 422/70 |
| 0031432 | 3/1981 | Japan | 436/178 |
| 0069251 | 4/1982 | Japan | 436/161 |
| 2045638 | 11/1980 | United Kingdom | 210/656 |

Primary Examiner—Barry S. Richman
Assistant Examiner—Robert J. Hill, Jr.
Attorney, Agent, or Firm—Moonray Kojima

[57] ABSTRACT

Method and apparatus for analysis, by ion chromatography, of anions, in a sample solution, wherein accurate analysis of anions in the sample solution is obtained by passing carbonic acid, through a prescribed membrane, into the sample solution, thereby completely eliminating or sharply lessening the so-called water dip effect. The method and apparatus are further directed to enabling anions in the sample solution to be accurately analyzed by passing prescribed cations, through a prescribed membrane, into the sample solution, thereby depriving the sample solution of interfering anions otherwise abundantly present therein.

3 Claims, 15 Drawing Figures

METHOD FOR ANALYSIS OF ANIONS

This is a division, of application Ser. No. 385,570 filed June 7, 1982, now U.S. Pat. No. 4,533,518.

BACKGROUND OF THE INVENTION

1. Field of the Invention

This invention relates to method and apparatus for the analysis, by chromatography, of anions in a sample solution.

2. Description of the Prior Art

The term "ion chromatography" is used to described a highspeed chromatography directed mainly to inorganic ions which was disclosed by H. Small et al in 1975. It has already been reduced to practice and has been finding extensive use in applications to various various forms of microanalysis, such as analysis of ecological specimen. The inventors of the present invention, pursued their studies independently of the ion chromatography method discussed above, and have developed their own ion chromatography system (hereinafter referred to as "IC" system for short), which far surpassed the aforementioned ion chromatography system disclosed by Small et al. A patent application covering the "IC" system has already been filed under the title "Method and Apparatus for the Analysis of Anions in Sample Solution".

FIG. 1 is an explanatory diagram illustrating the construction of the aforementioned IC system, cited as a conventional example. The IC system, as illustrated in the diagram, is provided with an eluant solution reservoir 1, for storing an eluant solution which is an aqueous solution containing $Na_2CO_3/NaHCO_3$ in a concentration of the order of several mM/liter; a pump 2, for transferring, under pressure, the eluant solution, such as, to sample injection means 3; a sample injection means 3, for admitting (or automatically collecting) a prescribed amount of the sample solution delivered, such as, with the aid of a microsyringe and, at the same time, conveying this sample solution with the eluant solution from pump 2; a separation column 4, packed with anion-exchange resin; a decationizer means 5, formed of a first compartmet for receiving the eluant solution from separation column 4, a second compartment for receiving a scavenger solution, and a wall of a perfluorocarbon sulfonic acid type cation-exchange composition, such as NAFION (trademark for a product of DuPont) serving as a common partition between the first and second compartments; detector means 6, for receiving the eluant from the first compartment in decationizer means 5 and, at the same time, measuring the conductivity of the eluant solution; a recorder 7, for displaying a chromatogram in accordance with an output signal from the detector 6; a scavenger solution reservoir 8, for storing a scavenger solution formed of a prescribed solvent, such as, for example, dodecylbenzene sulfonic acid; a pump 9, for transferring, under pressure, the scavenger solution from scavenger solution reservoir 8, to the second compartment in decationizer means 5; a reservoir 10 for storing a liquid already measured and flowing out of detector 6; and a reservoir 11, for storing the scavenger solution flowing out of the second compartment of decationizer means 5. The separation column 4, decationizer means 5, and detector 6 are, more often than than not, kept in a constant temperature bath 12, which is maintained at a prescribed temperature.

In the conventional ion chromatography (IC) system, above descibed, when the eluant solution $Na_2CO_3/NaHCO_3$ in eluant solution reservoir 1, is transferred via pump 2, sample injection means 3, and separation column 4, to decationizer means 5, it is converted to $H_2CO_3$ at decationizer means 5, in consequence of cation exchange of $Na^+$ and $H^+$. The aqueous solution of this $H_2CO_3$ retains a state of equilibrium as indicated by the following formula (1)

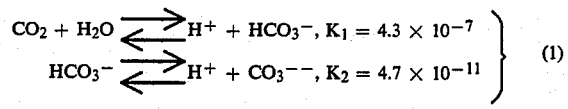

$$\left. \begin{array}{l} CO_2 + H_2O \rightleftharpoons H^+ + HCO_3^-, K_1 = 4.3 \times 10^{-7} \\ HCO_3^- \rightleftharpoons H^+ + CO_3^{--}, K_2 = 4.7 \times 10^{-11} \end{array} \right\} \quad (1)$$

and has a certain degree of conductivity. For example, the conductivity of an eluant solution of 4 mM $Na_2CO_3$/4 nM $NaHCO_3$, when measured after having passed through decationizer means 5, is found to be about 20 to 30 $\mu s/cm$.

When a sample solution composed preponderantly of water is introduced from sample injection means 3, the ions in the sample solution are retained in separation column 4, for a prescribed length of time and the water is not retained in separation column 4, but is passed through separation column 4. This water is not affected in any way either in decationizer means 5, but is passed therethrough. Of all the components of the sample solution, water is the first to reach detector 6.

On the other hand, the eluant solution exiting from decationizer means 5, contains carbonic acid, as described above, and has a conductivity of about 20 to 30 $\mu s/cm$. When water reaches detector 6 while the eluant solution is still in detector 6, and recorder 7 is drawing a base line of a chromatogram, the conductivity is lowered by the water. Consequently, a negative peak begins to appear in the chromatogram. This peak is ascribable to the water. This phenomenon, thus, is called a "water dip".

When the ion chromatograph system is used for experiment by injecting 100 $\mu l$ of a sample solution having water as a main component and containing 50 ppb of $F^-$, 100 ppb of $Cl^-$, 150 ppb of $NO_2^-$, 300 ppb of $PO_4^{3-}$, 100 ppb of $Br^-$, 300 ppb of $NO_3^-$, and 400 ppb of $SO_4^{2-}$ (hereinafter referred to as "experiment solution") through sample injection means 3, a chomatogram, such as shown, in FIG. 2, is obtained on recorder 7.

From FIG. 2, it is noted that while $F^-$ and $Cl^-$ barely produce output signals of the order of only 0.002 to 0.003 $\mu s/cm$ per ppb, water produces a peak output signal of as high as 0.8 $\mu s/cm$, indicating that water has a significant effect upon the chromatogram. The peak of water shows the so-called tailing phenomenon. Due to this phenomenon, coupled with the fact that the peaks of $F^-$ and $Cl^-$, which have brief retention periods, appear immediately after the peak of the water, there arise a significant problem, namely, that the highly sensitive measurements of $F^-$ and $Cl^-$ become infeasible. To avoid the various above discussed problems, there has been suggested a method whch eliminates the "water dip" by adding to the sample solution, a prescribed amount of $Na_2CO_3/NaHCO_3$, in advance thereby substantially equalizing the $Na_2CO_3/NaHCO_3$ concentration in the sample solution and that in the eluant solution.

This method, however, has disadvantange in that, the Na$_2$CO$_3$/NaHCO$_3$ reagent to be used must be tested for its purity, in advance of the addition to the sample solution, and the sample solution itself must be used in large amounts. The so-called concentration column method involves injection a large amount of the sample solution, allowing all the anions in the sample solution to accumulate in a concentration column, and consequently enabling the measurement of the anions to be effected with sensitivity 10 to 100 times the ordinary sensitivity. When the Na$_2$CO$_3$/NaHCO$_3$ is added to the sample solution until the concentration thereof equals that in the eluant solution, however, this method cannot be used, because the anions subjected to measurement are no longer retained in the concentration column. Furthermore, since practically all of the sample solutions given to be analyzed by ion chromatography have water as their main component, there is great demand for A solution to the above discussed and other problems of "water dip".

There exists a problem apart from the above discussed problem of water dip. When a sample, such as an organic specimen, which contains a trace amount of NO$_2^-$ in conjunction with a large amount of Cl$^-$, is analyzed for trace anion, accurate measurement of the trace anion becomes difficult because of the peak of trace anion (such as NO$_2^-$) is either affected abnormally or prevented from appearing at all by the interference offered by the peak of the large amount of anion (such as Cl$^-$).

SUMMARY OF THE INVENTION

Accordingly, this invention has been produced in view of the disadvantages suffered by the conventional ion chromatograph as described above. The primary object of this invention is to provide method and apparatus for the analysis of anions in a sample solution composed predominately of water, which permits the anions in the sample solution to be measured quickly and accurately by completely eliminating or notably lessening the "water dip".

This invention attains the primary object by injecting a prescribed amount of a smaple solution, as carried in a eluant solution, into a separation column, removing cations from the effluent from the separtion column, and thereafter passing either carbon dioxide or carbonic acid into the sample solution through a membrane which is pervious to carbon dioxide gas or carbonic acid, and impervious to anions.

A second object is to provide a method and apparatus for analysis of anions, which permits anions of interest to be quickly and accurately analyzed without being affected by interfering anions abundantly coexisting in the sample solution.

This invention attains this second object by passing prescribed cations through a cation-exchange membrane into the effluent which is discharged from the separation column and subsequently deprived of cations, thereby causing the added cations to be combined with anions abundantly contained in the effluent.

DETAILED DESCRIPTION OF PREFERRED EMBODIMENTS

Figure 1:
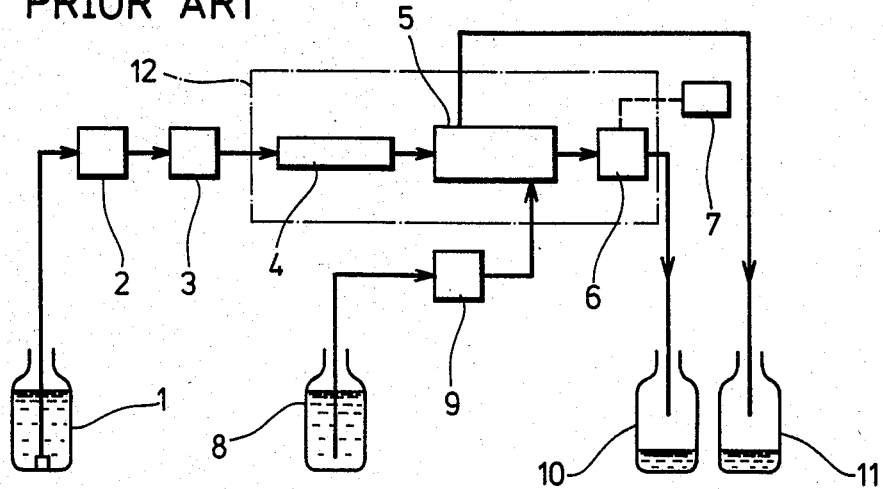
FIG. 1 is an explanatory diagram illustrating a conventional ion chromatography system.

In the drawings, various parts have the same numerical designations. These numeral designations and parts are: 1,8,10,11,14 and 16 are reservoirs; 2,9 and 15 are pumps; 3 is a sample injection means; 4 is a separation column; 5 is a decationizer means; 6 is a detector; 7 is a recorder; 12 is a constant temperature bath; 13 is a "water dip" remover; 13' is a selective deanionizer means; 131 is a membrane; 131' is a cation-exchange membrane; 132 is a tube; 133 and 134 are lids; and 135 and 136 are compartments.

Figure 3:
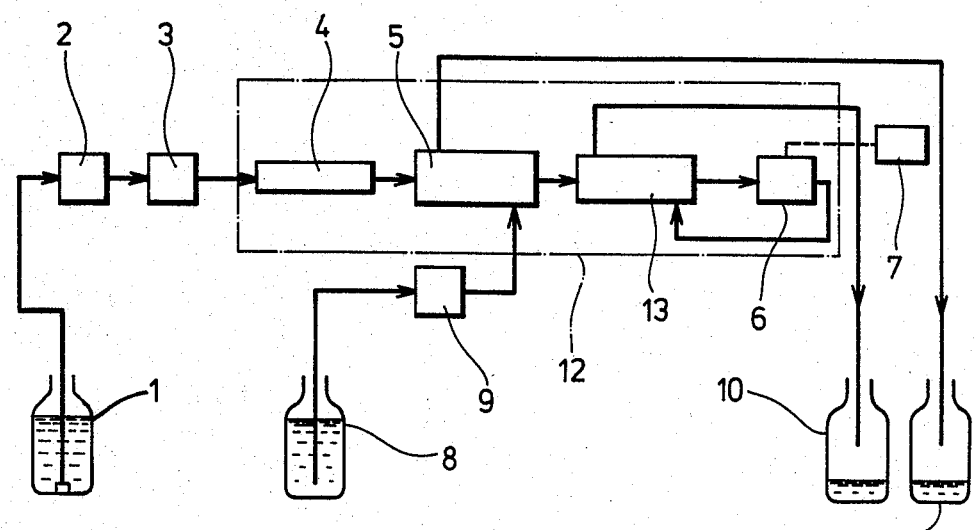
FIG. 3 depicts a pictorial diagram of an illustrative embodiment of the invention.

In FIG. 3 the same parts as shown in FIG. 1, and already discussed in detail hereinabove, have the same numbers and for the sake of clarity and to avoid useless duplication of discussion, will be omitted from discussion. In addition to the parts described in FIG. 1, there is provided a "water dip" removing device 13, comprising a third compartment for receiving effluent from the first compartment of decationizer means 5, a fourth compartment for receiving a prescribed liquid containing carbon dioxide gas or carbonic acid in substantially the same concentration as the effluent from the third compartment, and a membrane pervious to carbon dioxide or carbonic acid and impervious to anions and serving as a common wall between the third and fourth compartments.

The embodiment is constructed so that the effluent from the third compartment is guided to a detector 6, such as in the manner to be described hereinbelow; there to be tested for conductivity; then led to the fourth compartment of the "water dip" removing device 13; and thereafter to be discharged into a reservoir 10.

Figure 4:
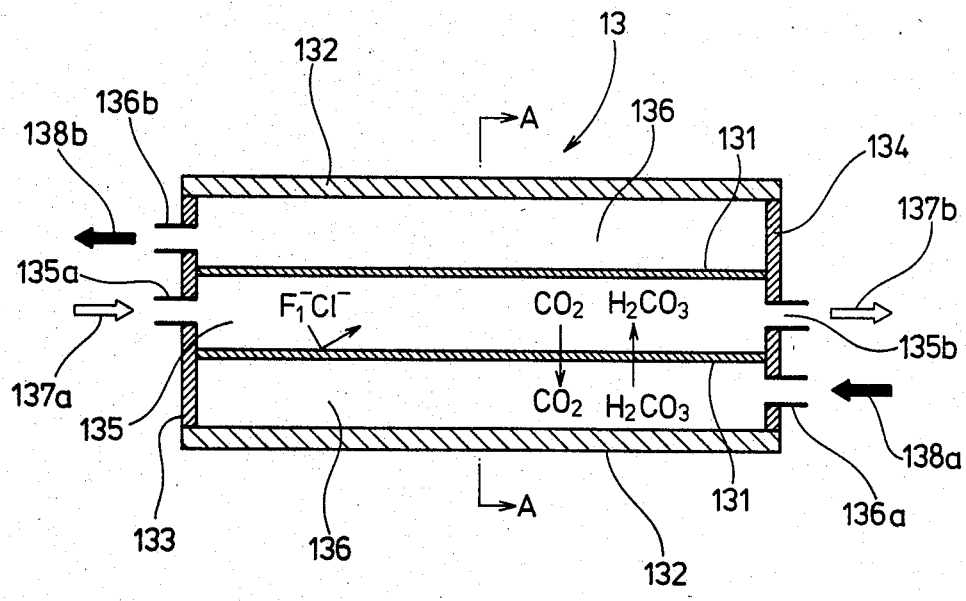
FIG. 4 is a cross sectional view taken in the axial direction of a carbonic acid replenishing device.
Figure 5:
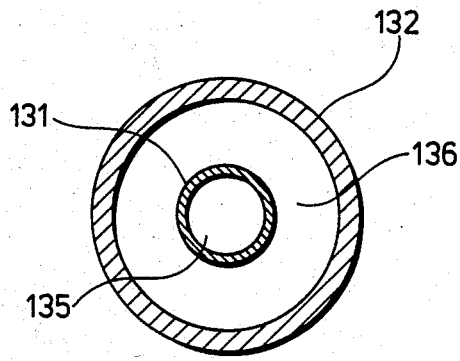
FIG. 5 is a cross sectional view taken along line A—A in FIG. 4.

FIG. 4 is a cross section taken in the axial direction of the "water dip" removing device 5. FIG. 5 is a cross sectional view taken along line A—A in FIG. 4. In these figures, there is provided a fine tube (preferably having an inside diameter of not more than 0.5 mm) of membrane 131 is made of such a material, for example, as NAFION (a trademark for a product of DuPont) and is impervious to anions, such as F$^-$ and Cl$^-$ and pervious to carbon dioxide gas or carbonic acid. A tube 132 encircles the membrane 131 to define an annular space of a suitable thickness surrounding the membrane 131, so as to form, for example, a coaxial tube, as depicted. Lide 133 and 134 close the opposite ends of the coaxial tube, to form third compartment 135 and fourth compartment 136, which are independent of each other and having a membrane 131 therebetween. Inlet 135a and outlet 135b enable third compartment 135 to communicate with ambient space. Inlet 136a and outlet 136b enable the fourth compartment 136 to communicate with ambient space.

Effluents 137a and 137b (designated by arrows) exit from the first compartment of decationizer means 5 (see FIG. 3) and effluents 138a and 138b (designated by arrows) exit from detector 6 to be led out further. The shapes of the membrane 131 and outer tube 132 are not limited to those slender cylinders shown in FIG. 5, but may be varied as desired. For example, they may be of elliptical cross section.

The effluent to be led to fourth compartment 136 of "water dip" removing device 13 is not limited to liquid discharge from detector 6. It may be supplied to the fourth compartment 136 through a different flow path (such as an independent flow path used exclusively).

Operation of the illustrative embodiment of FIG. 3 is as follows. By operation of pump 2, the eluant solution in eluant solution reservoir 1 is transferred in a flow volume of about 2.0 ml/min, for example, through sample means 3→separation column 4→first compartment of decationizer means 5→third compartment 135 of "water dip" removing device 13→detector 6→fourth compartment 136 of "water dip" removing device 13→reservoir 10. When pump 9 is operated, the scavenger solution in scavenger solution reservoir 8 is transferred in a flow volume of, for example, about 2 ml/min, through the second compartment in decationizer means 5 to reservoir 11.

If, in this condition, 100 μl of the experiment solution is collected, as a sample solution, in sample injection means 3, this sample solution mingles into the current of the eluant solution, and thus, is carried to separation column 4. At the separation column 4, the ions in the sample solution are subjected respectively to prescribed manners of separation.

Thereafter, the sample solution is led via decationizer means 5 and "water dip" removing device 13 to detector 6. At "water dip" removing device 13, illustrated in FIG. 4, therefore, the eluant solution supplied from detector 6 and containing carbon dioxide or carbonic acid is flowing through fourth compartment 136 and producing a concentration gradient by the time water in the sample solution reaches third compartment 135. As a result, the carbon dioxide gas or carbonic acid will pass through membrane 131 into the third compartment 135 and lend itself to uniformizing the concentration.

In contrast, the anions, such as $F^-$ and $Cl^-$ which are contained in the sample solution are incapable of permeating the membrane 131, and thus, have no possibility of adversely affecting the condition of separation. Since the water which reaches detector 6 in FIG. 3, has had carbon dioxide gas or carbonic acid added thereto, in advance by "water dip" removing device 13, the "water dip" is either completely eliminated or notably lessened to a point where no hindrance is encountered by the required measurement of anions.

Figure 6:
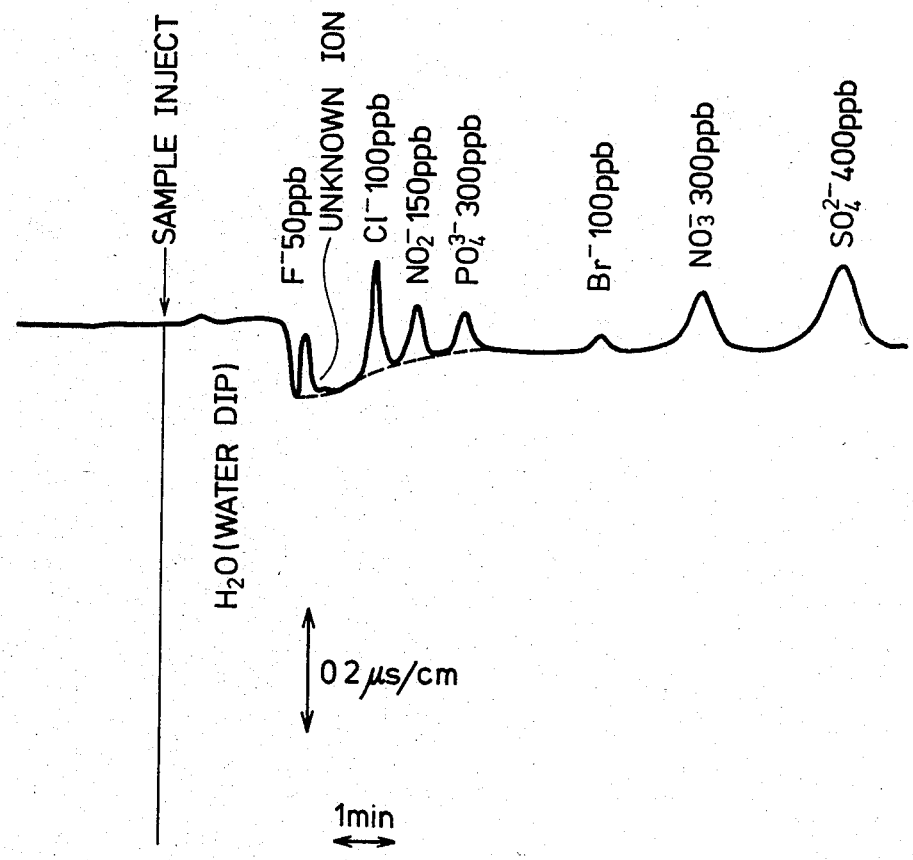
FIG. 6 is a chromatogram obtained by use of the embodiment of FIG. 3.

When "water dip" removing device 13 was produced by using as membrane 131, a NAFION sheet drawn and rolled in a tube measuring 0.4 mm in inside diameter, 0.55 mm in outside diameter, and 5 m in length and using as the outer tube 132, a TEFLON tube having an inside diameter of 1 mm, and the system was operated to analyze 100 μl of the experiment solution as the sample solution the chomatogram shown in FIG. 6 was obtained on recorder 7.

Figure 2:
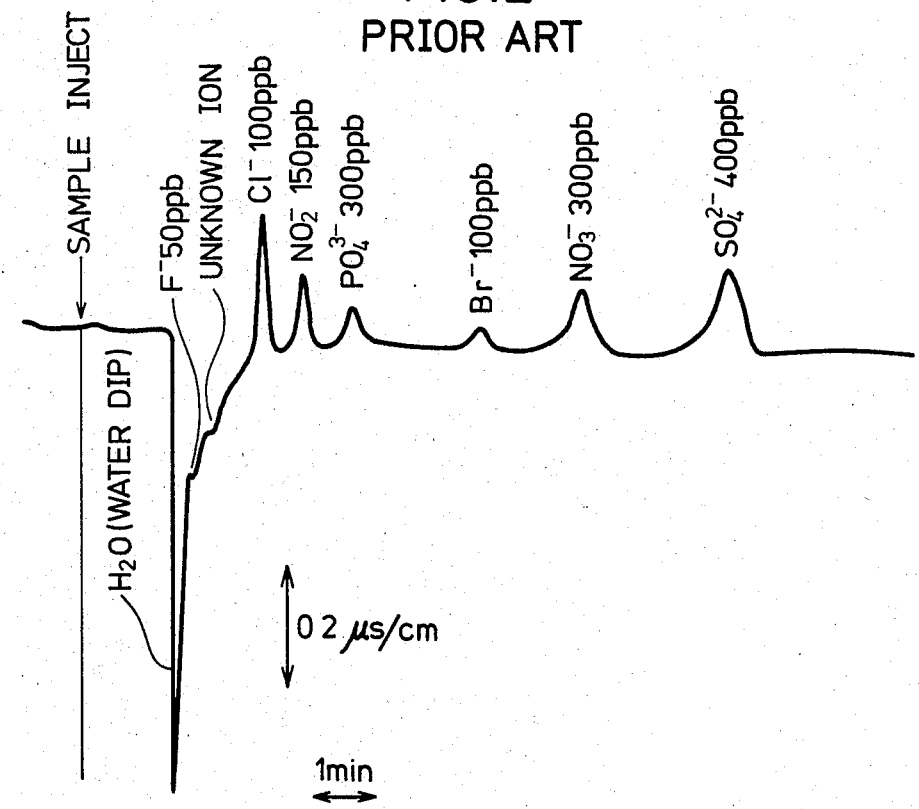
FIG. 2 is a chromatogram obtained by use of the system in FIG. 1.

As compared with the chromatogram shown in FIG. 2 obtained by using the conventional IC system, and using the same sample solution, the FIG. 6 chromatogram clearly indicated that the peak of $H_2O$ is remarkably diminished and the "water dip" was notably lessened sufficiently to permit thorough measurement of the $F^-$ present in trace amount. Complete elimination of the peak of $H_2O$ slightly appearing in the chromatogram of FIG. 6, can be easily accomplished by amply increasing the length of membrane 131 and tube 132. For practical purposes, however, it suffices to lessen the "water dip" to a point where the "water dip" will no longer hinder the measurement of anions of interest.

As described above, the embodiment of FIG. 3 notably lessens or completely eliminates the "water dip" by supplying carbon dioxide or carbonic acid to the portion involving "water dip" through the medium of a membrane pervious to carbon dioxide or carbonic acid and impervious to anions. Thus, it has an advantage, in that, the microanalysis of $F^-$ and $Cl^-$ which has defied effective measurement in the prior art, by such means as the conventional ion chromatography systems, can now be easily and quickly carried out using the invention.

Since the membrane is disposed within the "water dip" removing device and carbon dioxide gas or carbonic acid is passed thorugh this membrane into the sample solution, the present embodiment has another advantage, in that, the varying species of anions separated one from another, by the separation column, are scarcely disturbed.

Moreover, the liquid, which is introduced into fourth compartment 136, constituting itself an outer outer room for "water dip" removing device 13, is spent liquid, which has flowed through third compartment 135, constituting an inner room for "water dip" removing device 6, and has undergone test for conductivity in detector 6. Thus, the present invention enjoys yet another advantage, in that, the carbonic acid concentrations on the inside and outside of membrane 131 the "water dip" removing device 13 can be equalized without requiring any special liquid pump or reservoir.

Since this embodimetn either notably lessens or completely eliminates the phenomenon of "water dip", it has a further advantage, in that, the analysis of the trace anions in so-called pure water, which the conventional ion chromatography systems has performed only with great difficulty or has failed to perform at all, can be easily and accurately accomplished by the invention.

The embodiment of FIG. 3 involves a "water dip" removing device connected to a decationizer means comprising two compartments with a wall of cation-exchanging composition therebetween. The same effect of this invention can be obtained by connecting the "water dip" removing device to a packed suppressor, as described below.

Figure 7:
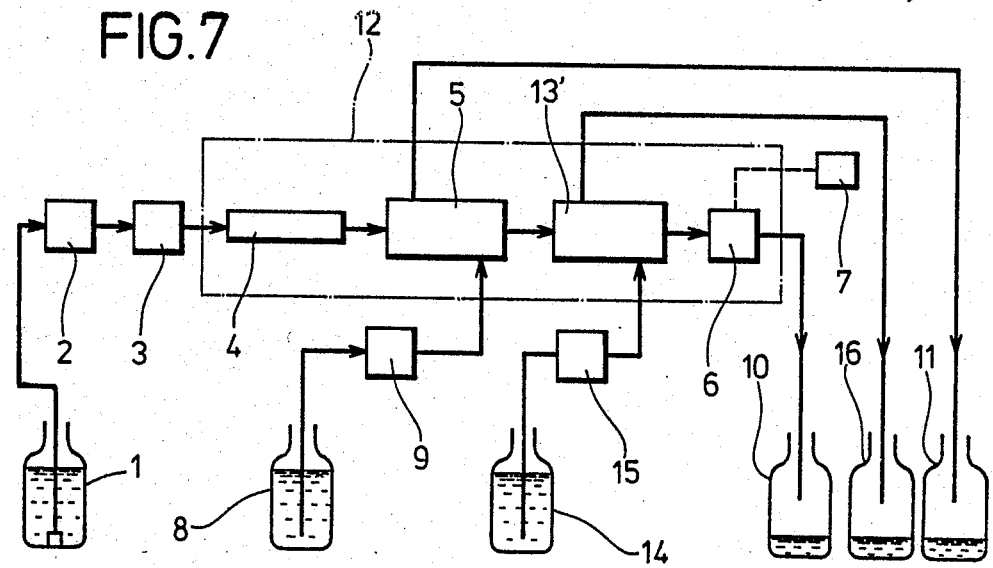
FIG. 7 depicts a pictorial diagram of another illustrative embodiment of the invention.

The embodiment of FIG. 7 shows similar parts as FIG. 1 labelled with the same numeral designations, and these parts will not be again hereat discussed for sake of clarity and to avoid unnecessary duplication. FIG. 7 depicts selective deanionizer means 13', comprising a third compartment for receiving and passing effluent from the first compartment in decationier means 5, a fourth compartment for receiving and passing a solution (such as $AgNO_3$ solution) containing a prescribed cation (such as $Ag^+$) and a cationexchange membrane shared by the mentioned two compartments; a solution tank 14 for storing the mentioned solution having the prescribed cation; a pump 15 for transferring under pressure the solution in reservoir 14, to the fourth compartment; and a reservoir 16 for storing the solution coming from the fourth compartment.

Figure 8:
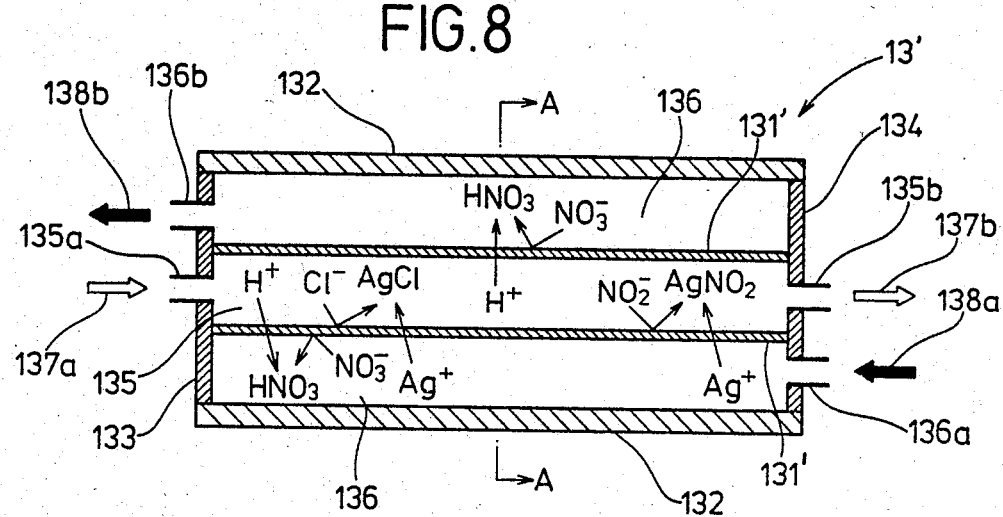
FIG. 8 depicts a cross sectional view taken along the axial dimension of a selective deanionizer means.
Figure 9:
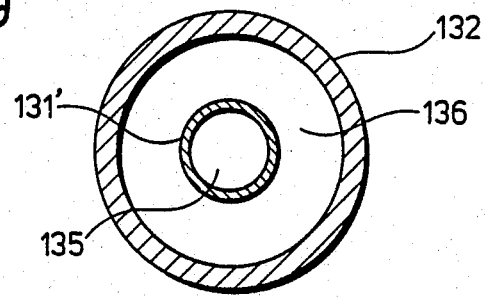
FIG. 9 is a cross sectional view taken along line A—A in FIG. 8.

FIG. 8 is a cross sectional view of a deanionizer means 13' of FIG. 7, taken along the axial direction; and FIG. 9 is a cross-section taken along line A—A in FIG. 8. Shown in these figures are a cation-exchange membrane 131' (preferably in the shape of a slender tube measuring, for example, 5 m in length, 0.40 mm in inside diameter, and 0.55 mm in outside diameter) made of, for example, the material NAFION, and being impervious to anions and being pervious to cations; a tube 132, such as of PTFE (polytetrafluoroethylene) encircling the cation-exchange membrane 131' and forming an annular space of a suitable thickness surrounding the membrane 131', so as to form a coaxial tube, as depicted. Lids 133 and 134 close the opposite ends of the coaxial tube and form thereby mutually independent third compartment 135 and fourth compartment 136. Inlet 135a and outlet 135b enable the third compartment 135 to communicate with ambient space. Inlet 136a and outlet 136b enable fourth compartment 126 to communicate with ambient space.

Effluents 137a and 137b (see arrows) originate in and flow out of the first compartment of decationizer means 5. Solutions 138a amd 138b (see arrows) are discharged from reservoir 14 by operation of pump 15. The shapes of the ion-exchange membrane 131' and tube 132 are not limited to those (such as slender tubes) shown in FIG. 9, but may be varied. For example, they may be elliptical in shape.

Operation of the embodiment of FIG. 7 is as follows. When pump 2 is operated, the eluant solution in eluant solution reservoir 1 is transferred in a flow volume of, for example, about 2.0 ml/min, through sample injection means 3→separation column 4→first compartment of decationizer means 5→third compartment 135 of selective deanionizer means 13'→detector 6→reservoir 10.

When pump 9 is operated, the scavenger solution in scavenger solution reservoir 8 is transferred in a flow volume of, for example, abourt 2.1 ml/min, through the second compartment of decationizer means 5 to reservoir 11. Then, when pump 15 is operated, the solution in solution reservoir 14 (such as, for example, a 0.001 mol $AgNO_3$ solution) is transferred in a flow volume of, for example, about 2.0 ml/min, through fourth compartment 136 of selective deanionizer means 13' to reservoir 16.

When, in this condition, 100 ml of a sample solution containing 5 ppm of $F^-$, 10 ppm of $Cl^-$, 15 ppm of $NO_2^-$, 30 ppm of $PO_4^{---}$, 10 ppm of $Br^-$, 30 ppm of $NO_3^-$, and 40 ppm of $SO_4^-$ (hereinafter referred to as "first experiment solution"), is collected in sample injection means 3, this first experiment solution is admixed into the surrent of the eluant solution, and is thus carried to separation column 4. In separation column 4, the varying species of anions in the first experiment solution are subjected to respectively specified manners of separation, then carried by the eluant solution to the first compartment in decationizer means 5, there to be deprived of cations contained therein. After the first experiment solution has been processed of cations as above described, it is forwarded as carried by the eluant solution through third compartment 135 of selective deanionizer means 13' to detector 6.

In the meantime, the solution (such as for example, a 0.001 mol $AgNO_3$ solution) is flowing through fourth compartment 136 of selective deanionizer means 13'. The ion-exchange group of cationexchange membrane 131' in selective deanionizer means 13' assumes Ag form, for example. The anions of interest such as $Cl^-$ and $Br^-$ in the first experiment solution which reaches third compartment 135 are bound with the prescribed cation such as $Ag^+$, with the result that the experiment solution has its conductivity lowered heavily or completely lost, as by being rendered sparingly soluble. Consequently, the peaks of the prescribed anions, such as $Cl^-$ and $Br^-$ disappear from the chromatogram displayed by recorder 7 in response to output signals from detector 6 and the peaks of the desired anions are obtained intact in spite of the prescribed interfering anions.

The functions of the selective deanionizer means 13' will be further described with reference to FIGS. 8 and 9. It will be assumed that an effluent 137a containing $H_2CO_3$, HCl, $HNO_2$, etc, is introduced through inlet 135a into third compartment 135 and a solution 138a which is an aqueous $AgNO_3$ solution, for example is introduced through inlet 136a into fourth compartment 136. Then, the cation-excchange membrane 131' is in an $Ag^+$ form. In third compartment 135, thus, effluent 137a has its strongly electrolytic components, HCl and $NHO_2$, dissociated into $H^+$, $CL^-$, and $NO_2^-$, and its weakly electrolytic component $H_2CO_3$, dissociated slightly into $H^+$, $HCO_3^-$, and $CO_3^{--}$. At the same time, the $Cl^-$ and $NO_2^-$ are virtually wholly converted into AgCl and $AgNO_2$ and the $HCO_3^-$ and $CO_2^{--}$ are virtually wholely converted into $AgHCO_3$ and $Ag_2CO_3$. As a result the effluent 137b which exits from outlet 136b is a solution containing $H_2CO_3$, $AgHCO_3$, $Ag_2CO_3$, AgCl and $AgNO_2$. Since AgCl, $AgHCO_3$ and $Ag_2CO_3$ are sparingly soluble and form precipitates, they show substantially no conductivity. On the other hand, $AgNO_2$ is soluble in water, and thus shows conductivity. When effluent 137b reaches detector 6, virtually no $Cl^-$ is detected but $NO_2^-$ is detected. Similarly, when effluent 137a contains $Br^-$ since $Br^-$ can be bound with $Ag^+$ to produce a sparingly soluble precipitate, AgBr, detectr 6 detects virtualy no $Br^-$ but detects the other anions.

Figure 10:
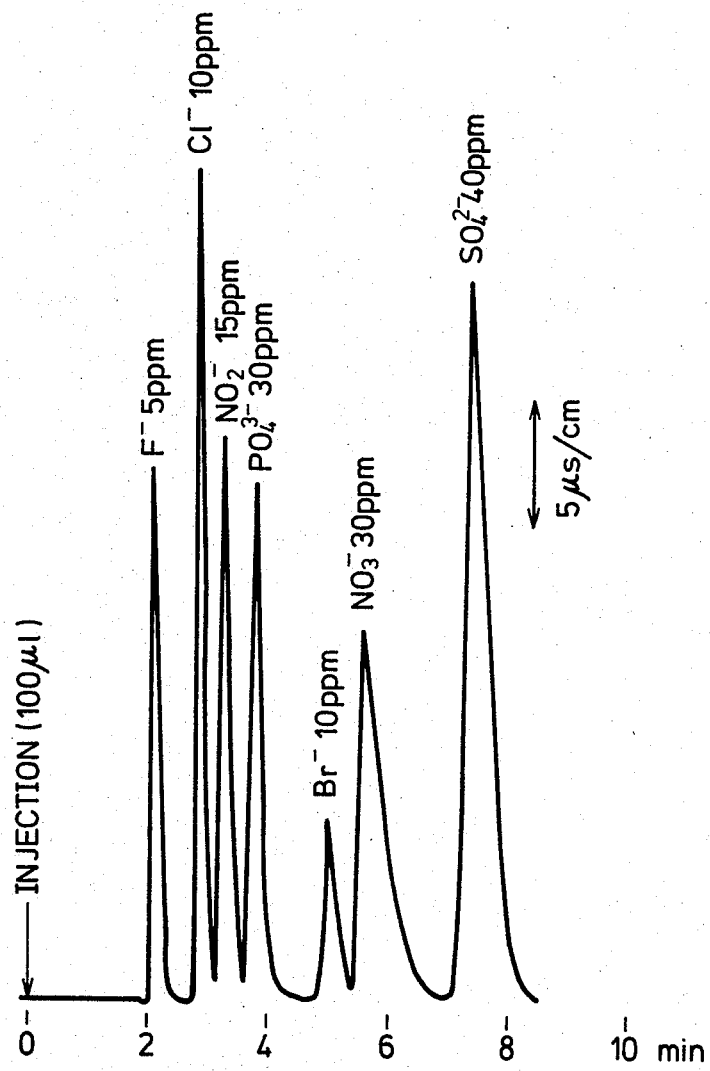
FIGS. 10 through 15, are chomatograms of test results using the invention and the conventional (IC) system of FIG. 1.
Figure 11:
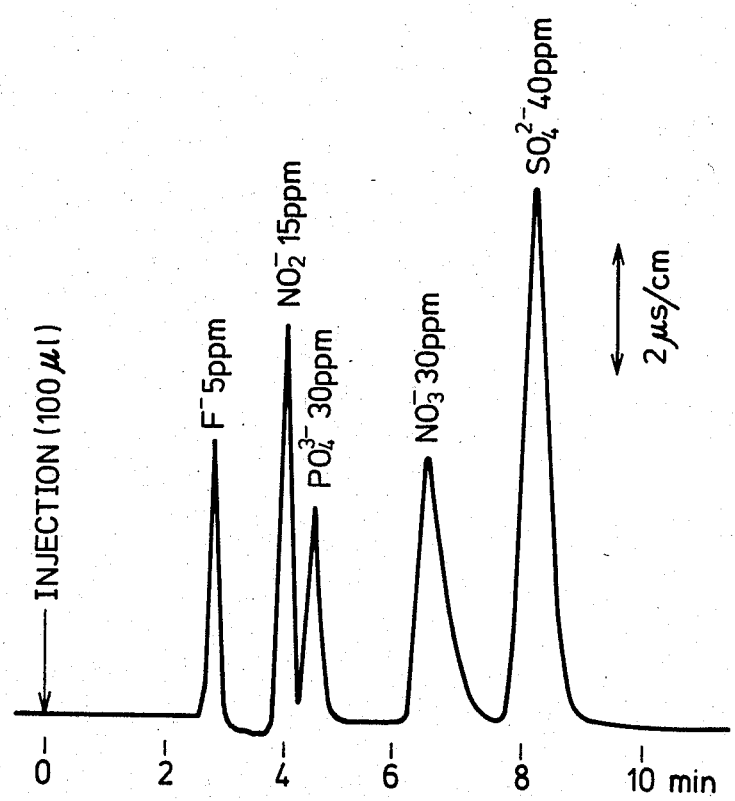
Figure 12:
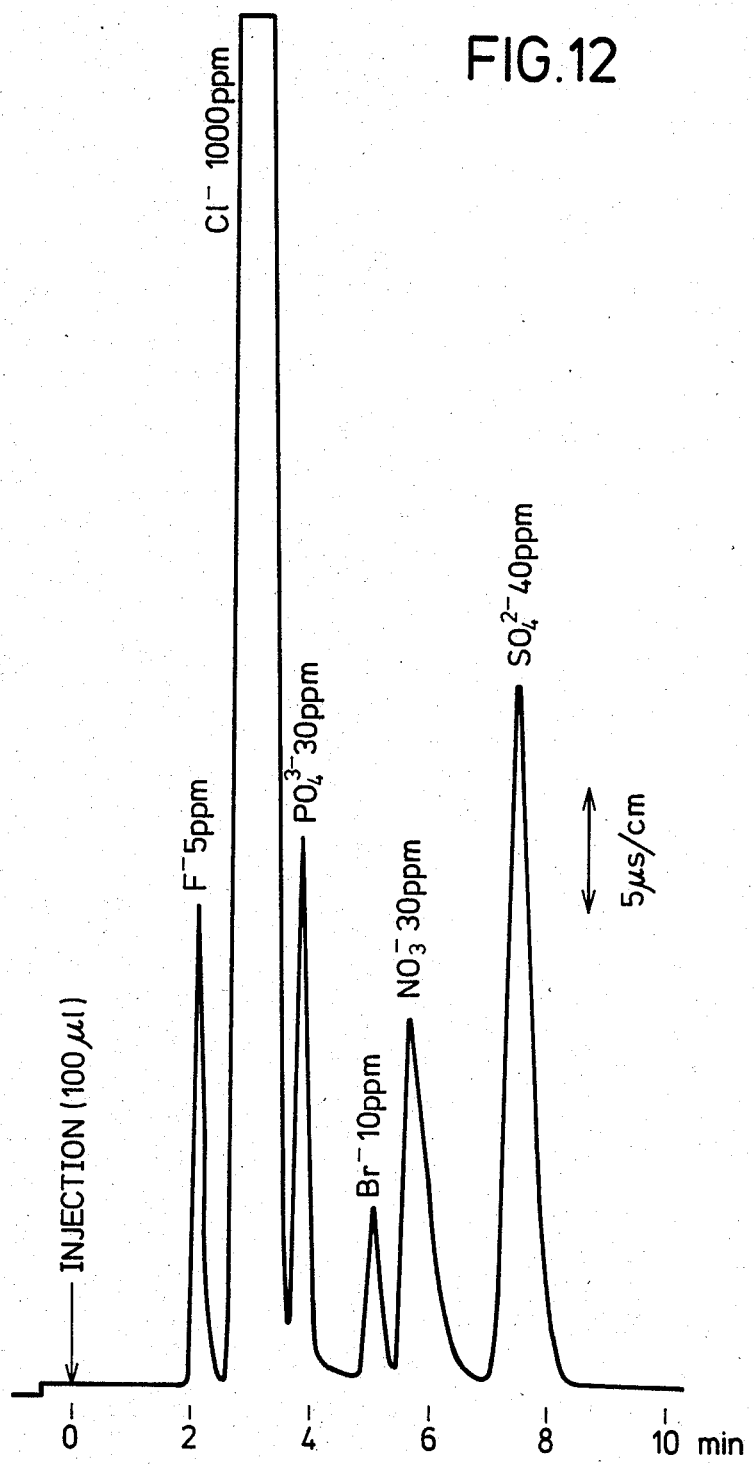
Figure 13:
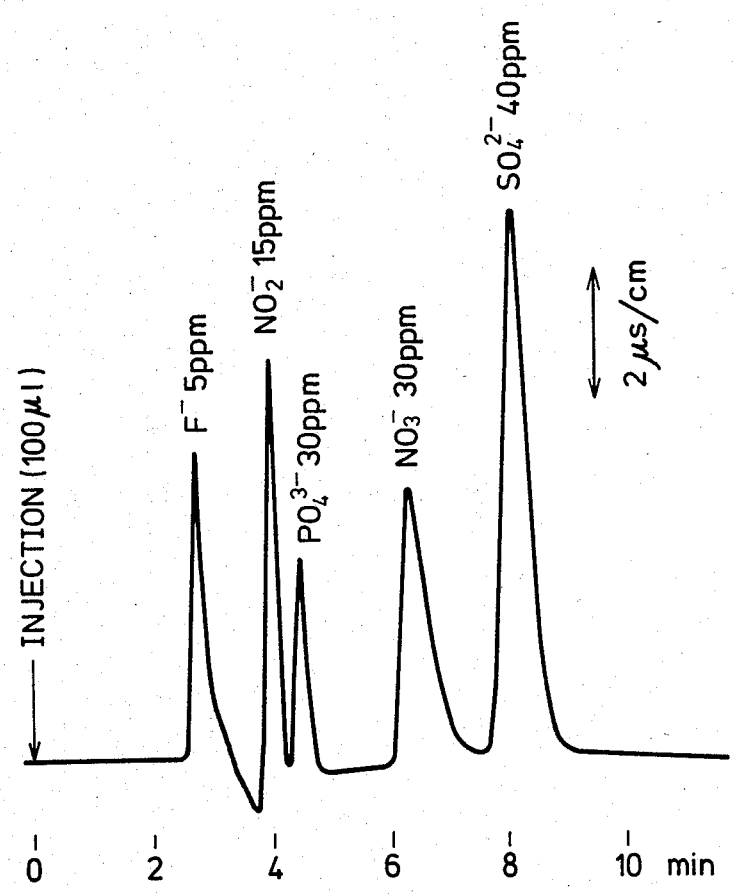
Figure 14:
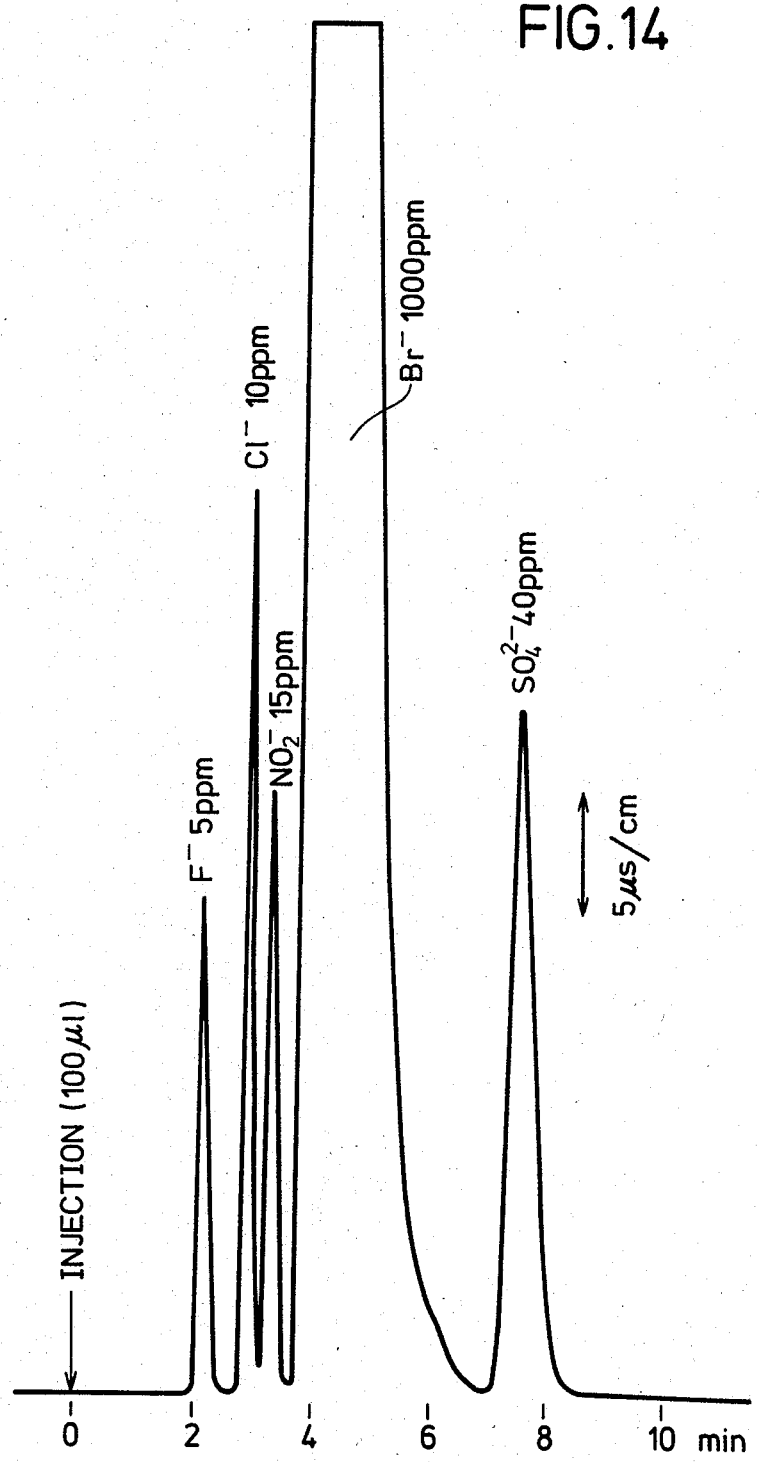
Figure 15:
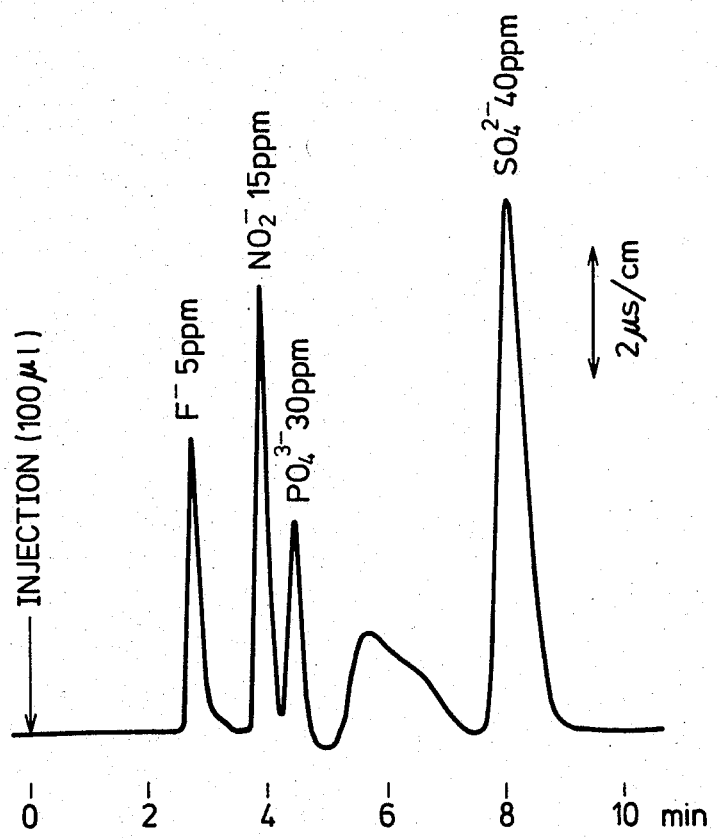

FIGS. 10 through 15 are chomatograms showing the results of experiments utilizing the techniques described above. FIGS. 10,12 and 14 are chromatograms obtained by using the conventional ion chromatographs system (IC) of FIG. 1 for the analysis of anions. FIGS. 11, 13 and 15 are chromatograms obtained by using the illustrative embodiment of FIG. 7 for the analysis of anions.

The experiments showing the results in FIGS. 10 and 11, used the mentioned first experiment solution as the sample solution. The experiments showing the results in FIGS. 12 and 13 used an experiment solution obtained by changing the concentration of $Cl^-$ alone in the first experiment solution to 1000 ppm (hereinafter referred to as "second experiment solution"). The experiments showing results in FIGS. 14 and 15 used another experimental solution obtained by changing the concentration of $Br^-$ alone in the first experiment solution to 1000 ppm (hereinafter referred to as "third experiment solution).

Comparison of the chromatograms of FIGS. 10 and 11, clearly shows that the embodiment illustrated in FIG. 7 eliminates the peaks of prescribed anions (such as for example $Cl^-$ and $Br^-$) with the peaks of other anions retained substantially intact.

Comparison of the chromatograms of FIGS. 12 and 13 also clearly shows that even with a sample solution, such as the second experiment solution, which contains a large amount of $Cl^-$ and a trace of $NO_2^-$, together, the embodiment of FIG. 7 permits a trace amount of NO$_2^-$ to be measured accurately.

Furthermore, comparison of the chromatograms of FIGS. 14 and 15 clearly shows that even with a sample solution, such as the third experiment solution, which contains a large amount of Br$^-$ and a trace amount of PO$_4^{---}$, together, the embodiment of FIG. 7 permits the trace amount of PO$_4^{3-}$ to be measured accurately.

As just described, the other illustrative embodiment of the invention can notably lower conductivities of prescribed anions by use of a selective deanionizer means. Thus, it enjoys an advantage in that trace amounts of anions contained simultaneously with large amounts of prescribed anions in a given sample solution are quickly and accurately analyzed without requiring the sample solution to subjected to an preliminary treatment.

The foregoing description is illustrative of the principles of the invention. Numerous modifications and extensions thereof would be apparent to the worker skilled in the art. All such modifications and extensions are to be considered to be within the spirit and scope of the invention.

What is claimed is:

1. A method for analysis of a trace amount of an anion in a sample solution comprising the steps of injecting a sample solution comprising water and an anion into a stream of eluant solution comprising alkali metal carbonates and bicarbonates; passing said sample solution, as carried in said eluant solution, to a separation column packed with an anion-exchange resin to separate the anion in said sample solution; passing an effluent solution from said separation column to a decationizer means packed with a cation-exchange composition to convert the alkali metal carbonates and bicarbonates to carbonic acid; then passing the effluent solution from said decationizer means to a water dip effect removing means wherein said water dip effect removing means comprises two compartments separated by a membrane pervious to carbon dioxide or carbonic acid and impervious to anions and wherein the effluent solution from said decationizer means is passed through one of said compartments and a solution of carbon dioxide or carbonic acid is passed through the outher of said compartments so as to pass carbon dioxide or carbonic acid into said effluent solution through the membrane; and thereafter passing the effluent solution from said water dip effect removing means to a conductivity detector and measuring the conductivity of the effluent solutin to determine the amount of said anion in the sample solution, whereby said water dip effect removing means substantially removes the impact of the water dip effect of water in the sample solution on conductivity of the effluent solution as measured by said conductivity detector.

2. The method of claim 1, wherein said carbon dioxide or carbonic acid solution comprises the effluent solution having been passed from said conductivity detector to said water dip effect removing means.

3. The method of claim 1 or claim 2, wherein said membrane is a fine tubular membrane.

* * * * *